US00PP34110P2

(12) United States Plant Patent
Hansen

(10) Patent No.: US PP34,110 P2
(45) Date of Patent: Apr. 5, 2022

(54) ***MONARDA* PLANT NAMED 'ELECTRIC NEON CORAL'**

(50) Latin Name: ***Monarda* hybrid**
Varietal Denomination: Electric Neon Coral

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,433

(22) Filed: Jun. 29, 2021

(51) Int. Cl.
*A01H 6/50* (2018.01)
*A01H 5/02* (2018.01)

(52) U.S. Cl.
USPC ..... Plt./455

(58) Field of Classification Search
USPC ..... Plt./455
See application file for complete search history.

*Primary Examiner* — Annette H Para

(57) ABSTRACT

The new and distinct cultivar of ornamental cultivar of hybrid ornamental Bee Balm plant named *Monarda* 'Electric Neon Coral' with deep-green, moderately-glossy, powdery mildew-tolerant foliage, flower heads of light coral-pink flowers from darker reddish-purple buds. The lower petal has darker reddish-purple spots on the inner surface. The bracts subtending inflorescences have deep reddish and wine coloration. The plant habit is compact and winter-hardy, useful in the landscape as a specimen, en masse, or as a containerized plant.

1 Drawing Sheet

Botanical designation and cultivar denomination:
Botanical classification: *Monarda* hybrid.
Variety denomination: 'Electric Neon Coral'.

STATEMENT REGARDING PRIOR DISCLOSURES UNDER 37 CFR 1.77(b)(6)

The first public disclosure of the claimed plant, in the form of a sale, was made by Walters Gardens, Inc. on Jun. 29, 2020. Prior to that, on Feb. 1, 2020 the claimed plant was displayed with a non-enabling photograph and brief description in a website operated by Walters Gardens, Inc., and on May 20, 2020 as a non-enabling photograph and brief description in the 2020-2021 Catalog by Walters Gardens, Inc., who obtained the plant and all information relating thereto, from the inventor. No plants of *Monarda* 'Electric Neon Coral' have been sold, in this country or anywhere in the world, nor has any disclosure of the new plant been made more than one year prior the filing date of this application, and such sale or disclosure within one year was either derived directly or indirectly from the inventor.

BACKGROUND OF THE INVENTION

The present invention relates to the new and distinct cultivar of Bee Balm, botanically known as *Monarda* 'Electric Neon Coral', and hereinafter also referred to solely by the cultivar 'Electric Neon Coral' or the "new plant." *Monarda* 'Electric Neon Coral' was the result of a controlled pollination in the summer of Jul. 24, 2014 in trial garden at a wholesale perennial nursery in Zeeland, Mich., USA. The female parent is a proprietary, unnamed, unreleased hybrid known as 12-27-8 and the specific male parent is a proprietary, unnamed, unreleased hybrid known as 12-59-12. The new plant was separated out for further evaluation in the summer of 2016 in the full sun trial gardens of the same nursery and assigned the breeder code 14-17-2. The new plant is the result of a planned breeding program of the inventor to produce new colors of flowers with superior mildew resistance, and improved compact habit. The new plant has been asexually propagated since 2016 by division and by basal stem cuttings at the same nursery in the greenhouses in Zeeland, Mich., and the subsequent generations of asexually propagated plants found to be stable and identical to the original selection.

BRIEF SUMMARY OF THE PLANT

*Monarda* 'Electric Neon Coral' is unique from its parents and all other Bee Balm plants known to the inventor. The nearest comparison cultivars known to the inventor are 'Bubblegum Blast' U.S. Plant Pat. No. 27,497, 'Electric Neon Pink' U.S. Plant Pat. No. 30,347 and 'Berry Taffy' copending U.S. Plant Patent Application. 'Bubblegum Blast' has lighter hot pink flowers and the habit is significantly taller. 'Electric Neon Pink' has flowers of a dark neon-pink color and is significantly taller in habit. 'Berry Taffy' has a similar height and a little narrower in width, but the flower color is hot raspberry pink. The female parent is more open and taller in habit than the new plant and darker pink in flower color. The male parent has a shorter habit and the flowers are lighter pink colored.

*Monarda* 'Electric Neon Coral' is distinct from all Bee Balm plants known to the inventor. The following are traits of the new plant that in combination distinguish it from all other Bee Balm known to the inventor:

1. Deep-green, moderately-glossy, powdery mildew-tolerant foliage;
2. Short, compact, clumping, upright mound that is winter-hardy habit;
3. Compact, light coral-pink flowers develop from darker reddish-purple buds for about a five-week-long period beginning late spring;

4. Lower petal has darker reddish-purple spots on the inner surface;
5. Bracts subtending inflorescences with deep reddish and wine coloration;
6. Flowering in dense verticils.

BRIEF DESCRIPTION OF THE DRAWINGS

The photographs of the new plant demonstrate the unique traits of *Monarda* 'Electric Neon Coral' and the overall appearance of the plant at three-years-old in the full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
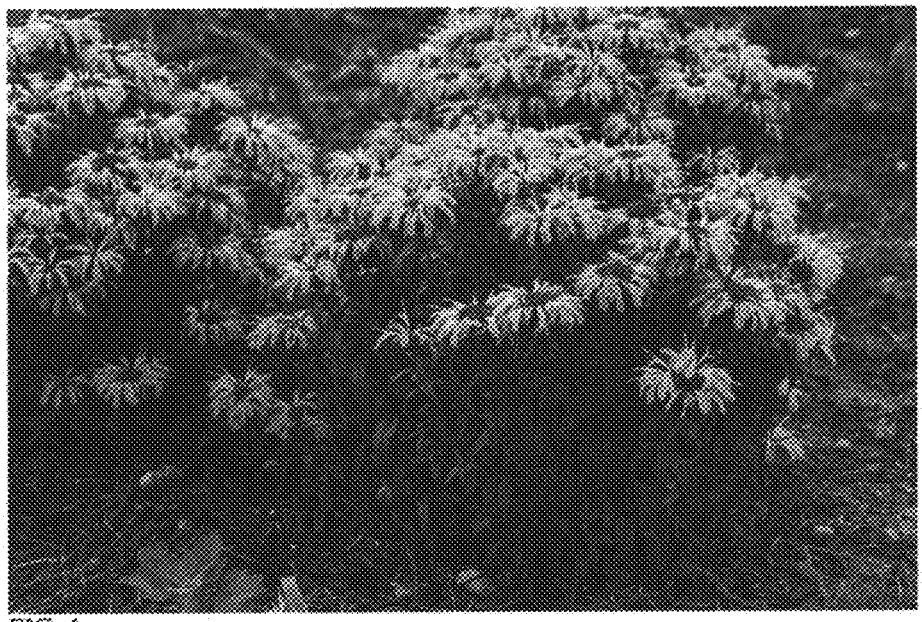
FIG. 1 shows the habit of the new plant in full flower.
Figure 2:
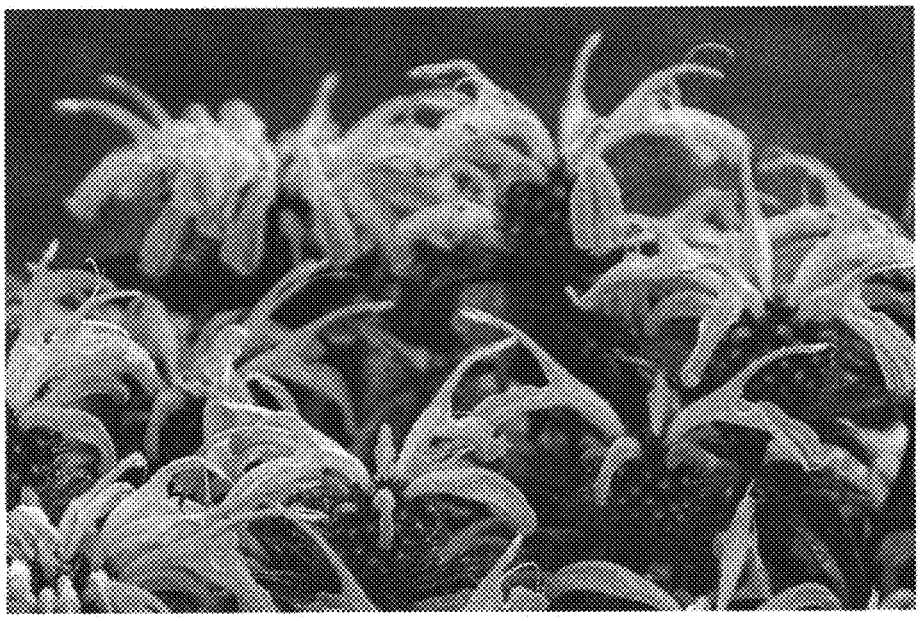
FIG. 2 shows a close-up of the flower of the new plant.

The following descriptions and color references are based on the 2015 edition of The Royal Horticultural Society Colour Chart except where common dictionary terms are used. *Monarda* 'Electric Neon Coral' has not been observed under all possible environments. The phenotype may vary slightly with different growing environments such as temperature, light, fertility, soil pH, moisture and maturity levels, but without any change in the genotype. The following observations and size descriptions are based on two-year-old plants grown in a trial garden at a nursery in Zeeland, Mich. with supplemental fertilizer and water as needed.

Botanical classification: *Monarda* hybrid;

Parentage: The female (seed) parent is 12-27-8, an unreleased proprietary hybrid; the male (pollen) parent is 12-59-12, an unreleased, proprietary hybrid;

Plant habit: Hardy herbaceous perennial, dense, upright mound, producing multiple stems spreading by short rhizomes near the base of the stems; foliage up to 40.0 cm tall, flowering to 43.0 cm tall and 47.0 cm wide; flowering begins late spring in Michigan and continuing for about 5 weeks;

Propagation: Stem cuttings;

Time to produce finished crop in 3.8 liter pots: About 7 to 9 weeks; moderate rate of growth;

Root: Fine, fibrous and freely branching; color creamy white to tan depending on soil type;

Leaves: Simple; lanceolate; opposite; margin serrated and ciliolate; puberulent above and below; moderately lustrous adaxial, matte to slightly lustrous abaxial; narrowly acute apex; cordate to rounded base; to about 8.2 cm long and 2.5 cm wide, average about 6.3 cm long and 2.3 cm wide near base;

Leaf color: Young expanding leaves adaxial between RHS 143A and RHS 144A with light overtone of nearest RHS 187A, abaxial nearest RHS 146B; older leaves adaxial nearest RHS NN137B with portions high in anthocyanins nearest RHS 187A, abaxial nearest RHS 147B with portions high in anthocyanins nearest RHS 187B;

Foliage fragrance: Pleasant lemony-herbal;

Veins: Pinnate; glabrous and slightly sunken adaxial, micropubescent and costate abaxial;

Vein color: Adaxial midrib variable, nearest RHS 183B and nearest RHS 147C, lateral pinnate veins and secondary veins between RHS 145A and RHS 146D; abaxial midrib variable, nearest RHS 147C and RHS 146C with frequent moderate to weak anthocyanin blush of nearest RHS 187B and with lateral pinnate veins nearest RHS 147C and secondary veins nearest RHS NN137B;

Petiole: Micro-puberulent, slightly concaved above; to about 6.0 mm long and 2.0 mm across at base;

Petiole color: Adaxial nearest RHS N186C and abaxial nearest RHS 146D with a slight to strong blush of nearest RHS N186C;

Stems: Quadrangular; puberulent; about 3.0 mm across at base; about 60 per plant; naturally branched at upper nodes; average 3.2 cm between nodes greater distally; 9 to 11 nodes per stem; average length about 22 cm;

Stem color: Nearest RHS 146C with heavy anthocyanin expression in high light nearest RHS 187A; nodes same color as surrounding stem;

Flowers: Single, bilabiate flowers arranged in mostly terminal verticils forming globular head about 75.0 mm across and 45.0 mm tall, opening from the center and progressing outwardly and down; attitude outwardly to upwardly; individual flowers to about 43.0 mm long to exserted stigma, 22.0 mm tall and about 5.0 mm across; individual flowers persisting about 5 days in Michigan; numerous, about 200 flowers per terminal head, fewer per axillary head; 105 inflorescences with open flowers at one time;

Flower fragrance: Moderately spicy;

Buds one to two days prior to opening: Narrowly oblanceolate, arcuate downward; about 25.0 mm long and 3.0 mm across and 12.0 mm tall;

Bud color: Basal 4.0 mm nearest RHS NN155B, distal and dorsal portion nearest RHS 61C, ventral region nearest RHS 62D;

Petals: Bilabiate; arcuate downward; basal 23.0 mm fused into tube; split in two in the distal 16.0 mm; abaxial glandular to puberulent, adaxial glabrous; self-cleaning;

Upper labium: Rolled or folded in middle portion, about 16.0 mm long from fusion to rounded apex, 5.0 mm tall, 2.5 mm across at base, about 4.0 mm across in middle when flattened;

Lower labium: About 16.0 mm long from fusion to apex, apex comprising three lobes including two side lobes about 1.0 mm long and 2.0 mm across with rounded apex, center lobe about 4.0 mm long with emarginate apex in the distal 0.5 mm;

Petal color: Upper labium abaxial surface nearest RHS 61C, adaxial surface proximally nearest RHS 62D and distally nearest RHS 61B; lower labium abaxial surface nearest RHS 61C with two long stripes nearest RHS 62D and spots from about 0.2 mm to 1.0 mm diameter nearest RHS 61B, adaxial nearest RHS 61D; corolla tube abaxial proximal 5.0 mm nearest RHS 62D, and distally nearest RHS NN155B, adaxial tube basal 5.0 mm nearest RHS NN155B and distally nearest RHS NN155B with light blush of nearest RHS 62D;

Androecium: Two; adnate inner corolla tube in basal portion;

*Filaments*.—Two; curved downward; adnate the inner corolla tube in the basal 17.0 mm and free in the distal 17.0 mm; about 0.5 mm diameter; color nearest RHS NN155D.

*Anther*.—Oblong elliptic, dorsifixed, longitudinal; 3.5 mm long by 1.0 mm wide; dorsal color nearest RHS 27D and ventral suture color nearest RHS N186D.

*Pollen*.—Abundant, elliptic to globose, less than 0.1 mm; color nearest RHS 18B.

Gynoecium: One; superior; about 42.0 mm long;

Pistil: One per flower; protruding about 6.0 mm beyond upper labium when mature;

Style: Cylindrical; glabrous; about 398.0 mm long and about 0.5 mm diameter; arcuate along upper labium; color nearest RHS 62C in distal 10.0 mm transitioning to nearest RHS NN155D in middle and basal portion;

Stigma: Unevenly bifid in the distal 2.0 mm with one portion 1.0 mm and the other 2.0 mm long, about 0.2 mm in diameter; color nearest RHS 64D;

Ovary: Conical; about 1.0 mm tall by 0.75 mm diameter; color nearest RHS 145D;

Calyx: Tubular to campanulate; consisting of five fused sepals; about 11.0 mm long and 4.0 mm diameter at apex;

Sepals: Five; acute apex; basal 10.5 mm fused forming calyx tube, free in distal 1.5 mm; margin micro-serrulate; about 12.0 mm long and 1.0 mm across at fusion; glabrous abaxial, glabrous adaxial except throat pubescent; persistent;

Sepal color: Adaxial and abaxial basal 2.0 mm nearest RHS 145D, middle adaxial portion nearest RHS 145C and abaxial potion nearest RHS 146D with veins nearest RHS 187B, distal 4.0 mm abaxial portion nearest RHS 187A with veins nearest RHS 187B, and distal 3.0 mm adaxial portion nearest RHS 146C with veins nearest RHS 187B;

Foliar bracts: Typically one set of five to seven large bracts on the outside per inflorescence and one set of six smaller bracts in the middle and one set of about 24 to 30 smaller narrow bracts on the inside below each inflorescence; outer bracts lanceolate with acute apex and attenuate sessile base, micro-ciliolate margin, glabrous adaxial, puberulent abaxial, flat to coarsely wavy, matte adaxial and abaxial, to 48.0 mm long and 18.0 mm wide in middle, color adaxial between RHS 187A and RHS N186B distally transitioning to nearest RHS NN137B in middle and RHS 145B at base, midrib nearest RHS 186A, color abaxial nearest RHS 138B with midrib nearest RHS 145C with variable blush of nearest RHS 187B; middle six bracts linear with narrowly acute apex and truncate base, ciliolate margin, glabrous adaxial and micro-puberulent abaxial, to about 22.0 mm long and 5.0 mm across near middle, adaxial color distal nearest RHS 187A, middle portion nearest RHS 137B with midrib nearest RHS 186A and base nearest RHS145D, abaxial color nearest 146C in middle with apex strongly blushed with RHS 187A and base nearest RHS 145D; innermost bracts linear, narrowly acute apex and truncate base, ciliolate margin, adaxial and abaxial glabrous, to about 17.0 mm long and 2.5 mm across at base, color variable, distally adaxial and abaxial nearest RHS 187B and proximally adaxial and abaxial transitioning to nearest RHS 145D at base;

Peduncle: Pubescent, stiff, strong, erect, quadrangular; to about 3.0 mm across and average 48.0 mm long above node; about 60 per plant; naturally branched at nodes;

Peduncle color: Variable between RHS 146C and RHS 187A;

Pedicel: About 2.0 mm long and 0.8 mm diameter; color nearest RHS 145B;

Fruit: Single, glabrous, lustrous, ellipsoidal nutlet; about 1.2 mm long and 0 7 mm wide; color nearest RHS 200C;

Hardiness: The new plant grows best with plenty of moisture and adequate drainage; hardy to at least from USDA zone 4 through 8.

Disease and pest resistance: Demonstrated greater than average powdery mildew tolerance in side by side comparison with other *Monarda*.

I claim:

1. A new and distinct cultivar of hybrid ornamental Bee Balm plant, *Monarda* 'Electric Neon Coral', as herein described and illustrated.

* * * * *